United States Patent [19]
Cordier et al.

[11] Patent Number: 5,840,989
[45] Date of Patent: Nov. 24, 1998

[54] CATALYST FOR THE HYDROGENATION OF NITRILES TO AMINES, PREPARATION PROCESS THEREOF AND HYDROGENATION PROCESS MAKING USE THEREOF

[75] Inventors: Georges Cordier, Francheville; Pierre Fouilloux, Caluire-et-Cuire; Nathalie Laurain, Lyons, all of France

[73] Assignee: Rhone-Poulenc Chimie, Courbevoie Cedex, France

[21] Appl. No.: 663,099

[22] PCT Filed: Dec. 16, 1994

[86] PCT No.: PCT/FR94/01476

§ 371 Date: Sep. 24, 1996

§ 102(e) Date: Sep. 24, 1996

[87] PCT Pub. No.: WO95/17959

PCT Pub. Date: Jul. 6, 1995

[51] Int. Cl.[6] .......................... B01J 25/02; C07C 209/00
[52] U.S. Cl. .......................... 564/490; 564/491; 564/492; 564/375; 502/301
[58] Field of Search ..................... 502/104, 301; 564/490, 491, 492

[56] References Cited

U.S. PATENT DOCUMENTS

| | | | |
|---|---|---|---|
| 2,948,687 | 8/1960 | Hadley et al. | 252/470 |
| 3,372,195 | 3/1968 | Little | 260/570.7 |
| 3,821,305 | 6/1974 | Bartatini et al. | 260/583 |
| 4,153,578 | 5/1979 | De Thomas et al. | 252/438 |
| 4,429,159 | 1/1984 | Cutchens et al. | 564/492 |
| 4,739,120 | 4/1988 | Zuckerman | 564/385 |

FOREIGN PATENT DOCUMENTS

| | | |
|---|---|---|
| 0 223 035 | 5/1987 | European Pat. Off. |
| 2 104 794 | 3/1983 | United Kingdom . |

OTHER PUBLICATIONS

Russian Chemical Reviews, Uspekhi Khimii, vol. 33, 1964.

*Primary Examiner*—José G. Dees
*Assistant Examiner*—Barbara Badio
*Attorney, Agent, or Firm*—Burns, Doane, Swecker & Mathis, L.L.P.

[57] ABSTRACT

The invention relates to a method of doping a Raney nickel catalyst doped with metals by the incorporation of the doping metals in the form of a complex into the alkaline attack medium. Also disclosed is a process for the hydrogenation of nitriles to amines using said catalyst.

44 Claims, No Drawings

5,840,989

CATALYST FOR THE HYDROGENATION OF NITRILES TO AMINES, PREPARATION PROCESS THEREOF AND HYDROGENATION PROCESS MAKING USE THEREOF

This application is a 371 of PCT/FR94/01476 filed Dec. 16, 1994.

The field of the invention is that of the catalytic reduction of nitriles to amines.

More precisely, it is in this instance a question of the catalytic hydrogenation of nitriles using catalysts of Raney nickel type, that is to say obtained by alkaline attack on a precursor Ni/Al alloy.

The present invention particularly relates to a catalyst for the hydrogenation of nitriles, especially of dinitriles to diamines, the said catalyst being of Raney nickel type doped with at least one element chosen from groups IIb and IVb to VIIb of the periodic classification.

Another subject of the present invention is a process for the preparation of a catalyst for the hydrogenation of nitriles to amines of doped Raney Ni type such as that targeted above.

The present invention additionally relates to a process for the hydrogenation of nitriles to amines which makes use of the catalysts considered above.

Within the meaning of the invention, nitriles denotes all aromatic and/or aliphatic mono- and dinitriles and, in particular but non-limitingly, the dinitriles resulting from dicarboxylic acids, preferably C3 to C6 dicarboxylic acids, such as adiponitrile, glutaronitrile, succinonitrile or malononitrile, optionally substituted by lower alkyl groups having from 1 to 6 carbon atoms, such as especially methyl or ethyl.

Raney nickels are catalysts which are widely used in industry and in the laboratory for hydrogenation reactions. They are prepared by alkaline attack on aluminium-rich Al/Ni alloys. The catalyst consists of agglomerates of nickel crystallites with a high specific surface and with a variable residual aluminium content.

In the field of catalysis in general and of hydrogenation catalysis in particular, the objectives ceaselessly targeted are, on the one hand, the optimization of the activity and selectivity of the catalyst with respect to the substrate to be hydrogenated and, on the other hand, the stability.

It is obvious that these three key parameters are indissolubly linked to the other constraints which are the ease of manufacture of the catalyst, its low cost price and the flexibility and convenience of its use in hydrogenation.

Thus, it has already been proposed to dope Raney nickel catalysts using promoters such as titanium, chromium, iron, cobalt, copper, molybdenum, tantalum, zirconium or other metals, with a view to improving their activity and/or their selectivity.

These promoters have the function of modifying the electronic and structural factors of Raney nickel. They are conventionally added to the Ni/Al alloy in the molten state, in accordance with a so-called "metallurgic" doping technique.

Patent FR 913 997 describes in particular the use of a Raney Ni, prepared from an Al/Ni alloy containing from 0.5% to 3.5% by weight of chromium with respect to the nickel, for the hydrogenation of adiponitrile to hexamethylenediamine.

The document B. N. Tyutyunnikov et al.—The Soviet Chemical Industry, No. 6, June 1991, as well as the article L. Kh. Freidlin et al.—Russian Chemical Reviews—Vol. 33, No. 6—Jun. 1964, among others, relate to the catalytic reduction of aliphatic nitriles (dinitriles) using Raney hydrogenation catalysts which have been promoted using metal doping agents.

Such catalysts are relatively difficult to obtain because they require the use of means for bringing the precursor alloy into the molten state and for maintaining it there. In addition, the known processes for obtaining these catalysts are relatively inflexible, especially as regards adjusting the amount of doping agents introduced into the alloy. In fact, mixing of the precursor alloy with the doping agent may sometimes not be homogeneous and may thus generate significant compositional variations or significant variations in the content of doping agent in the body of the catalyst. It should also be pointed out that phenomena which take place in the melt are not controlled. It is thus possible, in certain cases, to witness the formation of complex crystallographic structures which are harmful to the catalytic behaviour of the product.

Moreover, there exist certain limitations as regards the choice of the nature of the doping agent due to problems of compatibility with the nickel and the aluminium in the molten state.

It is also advisable to underline that some of the Raney Ni catalysts doped via the metallurgic route do not always make it possible to obtain satisfactory results as regards activity, selectivity and stability with time.

It should also be noted that the known catalysts described by Tyutyunnikov et al. and by Freidlin have relatively high residual aluminium contents, that is to say greater than 6% by weight. This does not favour the performance of the catalyst. Finally, it is observed that they are characterized by a doping agent/Ni ratio by weight which is greater than 8%.

The present invention aims to overcome the deficiencies and disadvantages of the doped Raney-type hydrogenation catalysts of the prior art.

The objective of the invention is thus to provide a doped Raney Ni hydrogenation catalyst which is easy and inexpensive to prepare and which satisfies the requirements of activity, selectivity and stability with time.

Another objective of the invention is to provide a process for the preparation of a Raney Ni hydrogenation catalyst which is simple and economic to implement.

Another objective of the invention is to provide a hydrogenation process in which a Raney Ni catalyst of the type of that targeted above is resorted to.

The Applicant company has, to its credit, demonstrated that, in order to achieve these objectives, it was advisable to carry out a chemical doping of the precursor alloy during the alkaline attack.

It follows that the subject of the present invention is a catalyst for the hydrogenation of nitriles to amines which is of Raney Ni type and which is doped with at least one element chosen from the elements from groups IIb and IVb to VIIb of the periodic classification, characterized in that its precursor alloy is substantially free from doping agent before the alkaline attack.

Within the meaning of the invention, the term "doping agent" corresponds to a chemical element deliberately added to the crude precursor alloy, immediately after its metallurgic synthesis, with a view to improving the catalytic properties.

Such a chemical doping greatly simplifies the preparation of the catalyst and significantly improves the quality of the catalysis.

In particular, this new catalyst makes it possible to increase the productivity and selectivity of the hydrogenation, while making it possible to decrease the level of appearance of undesirable hydrogenation by-products or impurities.

According to another aspect of the invention, this catalyst comprises an aluminium content, expressed by weight with respect to the weight of the nickel, of less than or equal to 6%, preferably of less than or equal to 5% and, more preferentially still, of between 2.5% and 4.5%.

Advantageously, the doping agent/Ni ratio by weight of this catalyst is between 0.05% and 10%, preferably between 0.1% and 5% and, more preferentially still, between 0.3% and 3.5%.

As regards the doping agent, it is preferably chosen from the following elements: titanium, chromium, zirconium, vanadium, molybdenum, manganese or zinc. Titanium, chromium and zirconium are particularly preferred.

In addition to nickel, aluminium and the doping agent(s), the catalyst can contain structural metal elements such as, for example, iron. This or these structural metal element(s) is/are present in an amount which is less than or equal to 10%, preferably less than or equal to 7% and, more preferentially still, less than or equal to 5.5% by weight in the finished catalyst.

The present invention also relates to a process for the preparation of a catalyst of Raney Ni type which can be used for the hydrogenation of nitriles to amines, the said catalyst being doped with at least one element chosen from the elements of groups IIb and IVb to VIIb of the periodic classification.

The preparation of a catalyst of Raney nickel type conventionally consists in subjecting a metal alloy comprising nickel and aluminium to an alkaline attack, leading to leaching of most of the aluminium.

In accordance with the invention, the starting precursor Ni/Al metal alloy was not subjected to doping via the metallurgic route. It is therefore substantially free from promoter metal element.

The precursor alloy is then subjected to the alkaline attack in the presence of the doping agent in the complexed form, which is intended to be chemically bound to the nickel.

Chemical doping according to the invention does not in any way complicate the conventional preparation of a Raney catalyst.

In addition, and in an entirely surprising and unexpected way, it appears that this simple arrangement of the process makes it possible to produce a catalytic structure of low cost price and outstanding performance.

In accordance with a preferred characteristic of the invention, the doping agent is introduced into the alkaline attack medium in the form of a solution which is preferably alkaline and, more preferentially still, of the same nature and substantially of the same alkaline assay as the attack medium.

The vehicle used for transporting the doping agent and for bringing it into contact with the precursor alloy is advantageously a complex of the doping agent with at least one chelating agent. It can be, for example, a salt of the doping agent, preferably one which is soluble in the alkaline attack medium. The chelating agent used is preferably selected from carboxylic derivatives, trienes, amines or other appropriate sequestering agents.

As regards the carboxylic acid derivatives, use will more readily be made of the following compounds: tartrate, citrate, ethylenediaminetetraacetate, gluconate or fatty acid carboxylates such as stearate, for example.

In accordance with a particularly advantageous embodiment, tartrate is selected as chelating agent of the chemical doping agent(s) of the Ni/Al alloy.

The doping elements under consideration are the same as those defined above.

As regards the chronology of the process, the doping agent is preferably introduced into the reactor from the beginning of leaching and in practice at the same time as the alloy to be treated.

Thus, in the case where the alkaline attack medium consists, for example, of 6N sodium hydroxide solution, the doping agent in the chelated form, and itself also dissolved in 6N sodium hydroxide solution, is brought into the reaction medium simultaneously with the alloy.

According to an implementational variant of the process according to the invention, chemical doping is carried out using two input metal elements chosen from groups IIb and IVb to VIIb of the periodic classification, preferably from the following elements: titanium, chromium, zirconium, vanadium, molybdenum, manganese or zinc. The combination of titanium and chromium is particularly preferred.

The amount of doping agent used during the alkaline attack depends on the final concentration of doping agent targeted in the catalyst. A person skilled in the art is entirely able to adjust the assay of the alkaline doping agent solution by taking into account the volumes used, the final targeted concentration of doping agent and the solubility limit of the doping agent/chelating agent complex in the alkaline medium under consideration.

In fact, it is preferable, under the reaction conditions, for the doping agent/chelating agent complex to be in the dissolved form during its introduction into the alkaline attack reaction medium.

As it is known that it is the solubility which sets the upper concentration limit of doping agent in the reaction medium, it may be indicated, to give an idea, that this concentration is, for example, greater than or equal to $10^{-5}$ mol/litre and preferably greater than or equal to $10^{-3}$ mol/litre of reaction medium at 25° C.

Introduction of doping agent apart, the process according to the invention is comparable to conventional methodologies for alkaline attack on Ni/Al precursor alloy to obtain a Raney Ni hydrogenation catalyst.

This process is one of the techniques which can be envisaged for preparing the new doped catalyst in accordance with the invention and described above.

The present invention also relates to a process for the hydrogenation of nitriles to amines, in which the new catalyst according to the invention is used.

This process is applied, more particularly but non-limitingly, to the nitrile substrates of formula (I):

$$NC-R-CN \tag{I}$$

in which R represents a linear or branched alkylene or alkenylene group having from 1 to 12 carbon atoms or a substituted or unsubstituted arylene or aralkylene or aralkenylene group.

Use is preferably made in the process of the invention of dinitriles of formula (I) in which R represents a linear or branched alkylene radical having from 2 to 6 carbon atoms.

Mention may be made, as examples of such dinitriles, of especially adiponitrile, methylglutaronitrile, ethylsuccinonitrile, malononitrile, succinonitrile and glutaronitrile and their mixtures, especially adiponitrile, methylglutaronitrile and ethylsuccinonitrile mixtures which arise from the same process for the synthesis of adiponitrile.

Introduction of the nitrile substrate, for example adiponitrile, into the reaction medium is carried out while observing a concentration of between 0.001% and 30% by weight with respect to the total weight (w/w) of the reaction medium and preferably between 0.1% and 20% w/w.

The strong base used is preferably chosen from the following compounds: LiOH, NaOH, KOH, RbOH, CsOH and their mixtures.

In practice, use is preferentially made of NaOH and KOH, for a good compromise between performance and price, although RbOH and CsOH give even better results.

The hydrogenation reaction medium is preferably liquid. It contains at least one solvent capable of dissolving the nitrile substrate to be hydrogenated, it being known that this conversion takes place more readily when the said substrate is in solution.

According to an advantageous embodiment of the process according to the invention, use is made of an at least partially aqueous liquid reaction medium. Water is generally present in an amount less than or equal to 50%, advantageously less than or equal to 20%, by weight with respect to the total reaction medium. More preferentially still, the water content of the reaction medium is between 0.1 and 15% by weight with respect to all the constituents of the said medium.

To complement or substitute for the water, it is possible to provide at least one other solvent, of alcohol and/or amide type. Alcohols which are more particularly suitable are, for example, methanol, ethanol, propanol, isopropanol, butanol, glycols, such as ethylene and/or propylene glycol, polyols and/or mixtures of the said compounds.

In the case where the solvent consists of an amide, it can be, for example, dimethylformamide or dimethylacetamide.

When it is used with water, the solvent, which is preferably alcoholic, represents from two to four parts by weight per one part by weight of water and preferably three parts per one part of water.

According to another preferred characteristic of the invention, the amine whose preparation is targeted by the process is incorporated in the reaction medium. It is, for example, hexamethylenediamine when the nitrile substrate is adiponitrile.

The concentration of the targeted amine in the reaction medium is advantageously between 50% and 99% by weight with respect to all the solvent included in the said reaction medium and, more preferentially still, is between 60% and 99% by weight.

The amount of base in the reaction medium varies according to the nature of the reaction medium.

When the reaction medium contains only water and targeted amine as liquid solvent medium, the amount of base is advantageously greater than or equal to 0.1 mol/kg of catalyst, preferably between 0.1 and 2 mol/kg of catalyst and more preferentially still between 0.5 and 1.5 mol/kg of catalyst.

In the case where the reaction medium comprises water and an alcohol and/or an amide, the amount of base is greater than or equal to 0.05 mol/kg of catalyst, is preferably between 0.1 and 10.0 mol/kg and more preferentially still between 1.0 and 8.0 mol/kg.

Once the composition of the reaction medium and the choice of the catalyst have been decided on, these two components are mixed and this mixture is then heated at a reaction temperature less than or equal to 150° C., preferably less than or equal to 120° C. and, more preferentially still, less than or equal to 100° C.

In concrete terms, this temperature is between room temperature (approximately 20° C.) and 100° C.

Prior to, simultaneously with or subsequent to the heating, the reaction chamber is brought to the appropriate hydrogen pressure, that is to say, in practice, between 0.10 and 10 MPa.

The duration of the reaction is variable according to the reaction conditions and the catalyst.

In a non-continuous operating mode, it can vary from a few minutes to a number of hours.

In a continuous operating mode, which it is entirely possible to envisage for the process according to the invention, the duration is obviously not a parameter which can be set.

It should be noted that a person skilled in the art can adjust the chronology of the stages of the process according to the invention, according to the operating conditions. The order given above only corresponds to a preferred, but non-limiting, form of the process according to the invention.

The other conditions which govern the hydrogenation (in continuous or non-continuous mode) in accordance with the invention involve technical arrangements which are conventional and known in themselves.

By virtue of all the advantageous arrangements mentioned above, the process of the invention makes it possible to hydrogenate nitrile substrates to amines in a selective, fast, convenient and economic way.

The hydrogenation of adiponitrile to hexamethylenediamine is particularly important for producers of polyamide-6,6, since this hydrogenated derivative is one of the basic monomers in this large-scale industrial synthesis.

Hydrogenation of dinitriles can also give access to aminonitriles. Thus, it is possible to hydrogenate only one of the two nitrile functional groups of adiponitrile to obtain aminocapronitrile. This last compound can be easily converted by cyclizing hydrolysis to caprolactam, which is the starting material of another large-scale industrial synthesis of a polyamide, namely polyamide-6.

It follows that this new hydrogenation catalyst, which is simple to prepare, economic, more selective, more active and more stable than the known catalysts, represents a noteworthy and appreciable technical advance in this field.

The invention will be better understood and its advantages and its implementational variants will clearly emerge from the examples which follow of the preparation of the new catalyst under consideration and of the application of the latter in the hydrogenation of adiponitrile to hexamethylenediamine.

EXAMPLES

The starting precursor alloys result from four typical phases of the nickel/aluminium binary mixture: $NiAl_3$, $Ni_2Al_3$, the $Al/NiAl_3$ eutectic and an $Al/NiAl_3$ proeutectic.

The alloys used in the examples are the following:

the commercial alloy Ni/Al=50/50 by weight ($NiAl_3$+ $Ni_2Al_3$ mixture, $Al/NiAl_3$ eutectic);

a pure homogenized $NiAl_3$ phase in which Ni/Al=42/58 by weight;

and an as-cast proeutectic in which Ni/Al=28/72 by weight;

and an as-cast eutectic in which Ni/Al=6/94 by weight.

MODE OF PREPARATION OF A CHEMICALLY-DOPED RANEY Ni CATALYST

1. PRODUCTION OF THE DOPING SOLUTIONS 1.1 Preparation of a titanium(IV) tartrate solution 120 g of L-tartaric acid are weighed into a 500 ml beaker. 340 g of distilled water are added. The mixture is stirred until the solid has completely dissolved.

Preparation of titanium tartrate is carried out in a glovebox purged a number of times with argon.

To do this, an amount of 12.59 g of $TiCl_4$ is poured, using a pipette, into the tartaric acid solution. A significant evolution of HCl, with a $TiO_2$ precipitate, is still observed. The amount of TiCl$_4$ introduced is weighed. The solution is very cloudy (white colour). The solution is decanted into a 1000 ml flask and the volume is made up to 1000 ml by addition of a 6N NaOH solution. The solution is still very cloudy. A number of hours are allowed to pass for equilibrium to become established. After 6 hours, a clear solution is available containing 3.16 g/l of Ti(IV).

1.2 Preparation of chromium(III) tartrate 140.16 g of L-tartaric acid are weighed into a 1000 ml Erlenmeyer flask. 267.72 g of distilled water are added. The mixture is stirred to dissolve the solid. 15.09 g of chromium (III) acetate hydroxide $(CH_3CO_2)_7Cr_3(OH)_2$ are then introduced using a spatula. The mixture is stirred until the solid has completely dissolved. 6N Sodium hydroxide solution is then added to a volume of 1000 ml.

The solution obtained assays 3.90 g/l of Cr(III).

2. PREPARATION OF THE RANEY Ni CATALYST

For the four types of Ni/Al precursor alloy used indicated above, the following methodology is used:

Stage 1: 300 ml of 6N sodium hydroxide solution are introduced at room temperature into a 2 l, round-bottomed, Teflon flask.

Stage 2: 10.00 g of alloy are weighed into a beaker.

Stage 3: The alloy is then introduced, using a spatula, into the sodium hydroxide solution at the rate of 10 g/h, care being taken that the average temperature of the medium does not exceed 50° C. (cooling by an ice-water bath).

Stage 3a: The alkaline solution containing the doping agent is simultaneously incorporated using a metering pump.

Stage 4: When all the alloy is introduced, it is necessary to wait until effervescence has finished (5 min).

Stage 5: Heating is carried out at reflux (temperature=108° C.) for 2 hours.

Stage 6: After refluxing for 2 hours, the round-bottomed flask is removed from the heating mantle and there is a wait of 5 min until boiling has ceased. A magnet is placed under the round-bottomed flask and the supernatant is removed after separation by settling of the solid phase.

Stage 7: 300 ml of 1N sodium hydroxide solution which is virtually boiling (approximately 85° C.) are introduced and the round-bottomed flask is shaken 3 or 4 times. A magnet is then placed under the round-bottomed flask and the solid is allowed to separate by settling. Finally, the supernatant is removed.

Stage 8: 300 ml of 6N sodium hydroxide solution which is virtually boiling (approximately 85° C.) are introduced and the mixture is brought to reflux for 2 hours.

Stage 9: idem Stage 6.

Stage 10: idem Stage 7 but with 300 ml of "boiling" 6N sodium hydroxide solution.

Stage 11: idem Stage 7 but with 300 ml of "boiling" 3N sodium hydroxide solution.

Stage 12: idem Stage 7 but with 300 ml of "boiling" 2N sodium hydroxide solution.

Stage 13: idem Stage 7 but with 300 ml of "boiling" 1N sodium hydroxide solution.

Stage 14: The solid is recovered in a flask and is stored in cold 1N sodium hydroxide solution.

The alkaline solution of Stage 3a can be that of Ti or Cr tartrate, the preparations of which are described in 1.1 and 1.2 above.

The amount of alkaline doping solution used is a function of the final targeted concentrations of doping agent.

Thus, with 10 g "of commercial alloy", use is made of 55.6 ml of a solution of Ti tartrate in 6N sodium hydroxide solution containing 3.6 g/l of Ti to obtain a final Ti/Ni ratio=1.20% by weight in the finished catalyst.

Various catalysts doped with Ti and/or with Cr were thus prepared from various alloys, with various doping agent/Ni concentrations in the finished catalyst.

EXAMPLES 1 TO 25

Hydrogenation of Adiponitrile (ADN) to
Hexamethylenediamine (HMD) Using Catalysts
According to the Invention and Comparative Tests
1 TO 4 Using Catalysts According to the Prior Art

1. EQUIPMENT, PRODUCTS USED AND METHODOLOGY 1.1 Equipment for non-continuous tests Use is made of a 150 ml autoclave made of 316 L stainless steel. This autoclave is equipped with a magnetic stirrer system (1500 rev/min, magnetic bar and counterblades) providing good gas/liquid transfer. Heating is carried out by means of a thermo regulated heating sleeve. The substrate to be hydrogenated is introduced via a steel dropping funnel surmounting the autoclave; it can also be introduced using a high-pressure pump in the case of a semi-continuous reactor. The hydrogen is stored under 5 MPa in a store equipped with a manometer connected to a recorder. It is pressure-released into the assembly at the constant pressure of the reaction. The kinetics of the reaction are monitored by recording the fall in pressure in the hydrogen store. Hydrogenate samples intended for analysis are withdrawn via a dip pipe equipped with a steel filter.

1.2 Products used 99.99% Adiponitrile (Rhône-Poulenc, MW=108.15).

99.99% Hexamethylenediamine (Rhône-Poulenc, MW=116.21).

99.995% U Hydrogen by volume.

99.8% Ethanol.

Distilled water.

98% Sodium hydroxide or 86% potassium hydroxide.

Catalyst: Raney nickel, chemically doped according to the invention with Ti and/or with Cr, prepared as described above or doped metallurgically with Cr or non-doped according to the prior art.

1.3. Progression of a typical test 1.3.1 Charges

Adiponitrile: 6.0 g (0.055 mol)

Hydrogen: excess (0.222 mol)

Reaction medium: 42 g of reaction solvent [HMD/H$_2$O/ ethanol]+alkaline base [NaOH]; the alkaline base represents 0.10% by weight of the reaction medium;

42 g of reaction solvent [HMD/H$_2$O]+KOH; the alkaline base represents 0.05% by weight of the reaction medium.

Catalyst: 0.40 g.

1.3.2. Procedure

An excess of Raney nickel slurry (1–2 g) is withdrawn, the catalyst is washed with six times 50 ml of distilled water and 0.40 g of catalyst is weighed exactly with a pycnometer. The wet Raney nickel is then introduced into the autoclave. For a catalyst mass of 0.40 g, the amount of water commonly entrained is of the order of 0.4 g. This water mass will be taken into account in the composition by weight of the reaction solvent of 60/30/10 in HMD/ethanol/water or 98/2 in HMD/water. The alkaline base is introduced with the amount of water necessary for adjusting the required water percentages. All these handlings must take place under an argon atmosphere in order to minimize carbonation of the solvent and oxidation of the catalyst.

The autoclave is then purged with nitrogen and with hydrogen. Finally, it is heated and maintained under 2.5 MPa of hydrogen. Recording of the pressure in the hydrogen store is begun and the ADN is rapidly added. When hydrogen consumption becomes zero, the reactor is left stirring for a further half-hour in order to better ensure that the reaction is finished. At the end of the test, a hydrogenate sample is withdrawn in order to determine the selectivity. The initial activity and a "mean activity" are deduced from the curve of hydrogen consumption as a function of time.

2. ANALYSES 2.1. Measurement of the activity

The slope at the beginning of the hydrogen consumption curve is proportional to the initial rate (Ri). This size is calculated by drawing up the quotient at the beginning of the number of moles of hydrogen consumed per unit of time corrected for the catalyst mass unit. The initial rate will be expressed in kmol of hydrogen consumed per kg of catalyst and per second.

In order for the behaviour of a catalyst to be well assessed, it is necessary to know if the initial activity is not detrimentally affected by premature ageing. This is why the mean reaction rate (Rm), which is the quotient of the number of moles of hydrogen brought into play to the total time of the reaction per catalyst mass unit and per second, is also measured.

The reproducibility of the test for the determination of Ri and Rm gives an uncertainty of less than 10%.

2.2. Measurement of the selectivity

At the end of the reaction, a hydrogenate sample is withdrawn and diluted approximately 40 times in isopropanol. This sample is quantitatively analysed by gas phase chromatography (GPC) using a semi-capillary column. The detector is a flame ionization detector. Quantitative determination of the by-products of the hydrogenation reaction of ADN is carried out by the internal standard method (undecane).

The list of the main by-products quantitatively determined is given below:

HMI: Hexamethyleneimine

AMCPA: Aminomethylcyclopentylamine

AZCHe: Azacycloheptene

NEtHMD: N-Ethylhexamethylenediamine

DCH: cis- and trans-Diaminocyclohexane

BHT: Bishexamethylenetriamine.

The selectivity (S) for HMD as a percentage is given by the relationship: 100—sum of the selectivities of the by-products. In fact, as HMD is used in the reaction solvent, it cannot be directly quantitatively determined very precisely. On the other hand, it has been verified that the by-products, taken as a whole, are all identified.

The selectivities for each of the by-products are represented by the molar percentage of the by-product formed with respect to the converted ADN. In all the examples and comparative tests carried out, the degree of conversion of the ADN (as well as that of the intermediate aminocapronitrile) is 100%.

When a compound does not reach its detection limit, the comment ND (not detected) will be carried in the tables of results.

The level of unsaturated products present in the hydrogenate can be evaluated by polarography.

3. RESULTS 3.1. Raney Ni catalysts doped with titanium

Hydrogenation with HMD/$H_2$O/ethanol/NaOH (Examples 1 to 16).

Table 1 below collates the results obtained in these examples as well as in a Comparative Test (Tc) 1 using a non-doped Raney Ni catalyst and Comparative Tests (Tc) 2 and 3 using Raney Ni catalysts metallurgically doped with chromium.

3.2. Raney Ni catalysts doped with chromium Hydrogenation with HMD/$H_2$O/ethanol/NaOH (Examples 17 to 20 and Comparative Test 4 with Raney Ni metallurgically doped with Cr).

3.3. Raney Ni catalysts doped with titanium and with chromium

Hydrogenation with HMD/$H_2$O/ethanol/NaOH (Examples 21 to 25).

Table 2 below collates the results obtained in Examples 17 to 25 and shows, on the one hand, that chromium is a doping agent which is as advantageous as titanium and, on the other hand, that the use of two doping elements is also entirely advantageous, as regards selectivity and removal of impurities. It is also noted that metallurgically-doped catalysts lead to higher selectivities for by-products, such as BHT or HMI in particular, than chemically-doped catalysts according to the invention.

3.4. Raney Ni catalyst doped with titanium

Hydrogenation with HMD/$H_2$O/KOH (Example 26).

starting alloy: Ni/Al=50/50 by weight 0.72% by weight of Ti/Ni in the catalyst 3.25% by weight of Al/Ni in the catalyst.

The following results were obtained:

Ri=46

Rm=4

S for HMD: 98.0%

S for HMI: 0.203%

S for AzCHE: 0.191%

S for DCH: 0.046%

S for AMCPA: 0.489%

S for BHT: 1.130%

TABLE 1

| Tests | Al/Ni Alloy % by wgt | Doping agent % by wgt/Ni | Al/Ni % by wgt | Ri | Rm | S % for HMD | S % for HMI | S % for AzCHe | S % for cis- + trans-DCH | S % for AMCPA | S % for NEtHMD | S % for BHT |
|---|---|---|---|---|---|---|---|---|---|---|---|---|
| Ex 1 | 50/50 | 0.54 Ti | 3.10 | 80 | 40 | 96.9 | 0.084 | 0.014 | 0.035 | 0.023 | 0.080 | 2.822 |
| Ex 2 | 50/50 | 0.72 Ti | 3.25 | 85 | 37 | 98.3 | 0.083 | 0.036 | 0.034 | 0.031 | 0.065 | 1.503 |
| Ex 3 | 50/50 | 0.90 Ti | 3.30 | 97 | 48 | 97.7 | 0.071 | 0.039 | 0.034 | 0.016 | 0.021 | 2.133 |
| Ex 4 | 50/50 | 1.20 Ti | 4.00 | 118 | 56 | 98.5 | 0.055 | 0.040 | 0.072 | 0.033 | 0.063 | 1.199 |
| Ex 5 | 50/50 | 1.75 Ti | 4.40 | 123 | 59 | 98.3 | 0.120 | 0.072 | 0.040 | 0.008 | 0.029 | 1.435 |
| Tc 1 | 42/58 | 0 | 2.00 | 11 | 3 | 78.2 | 4.981 | 1.038 | 0.061 | 0.029 | 0.099 | 8.791 |
| Ex 6 | 42/58 | 0.12 Ti | 2.43 | 19 | 6 | 93.2 | 1.559 | 0.789 | 0.067 | 0.023 | 0.061 | 4.276 |
| Ex 7 | 42/58 | 0.40 Ti | 2.60 | 49 | 22 | 95.8 | 0.303 | 0.056 | 0.016 | 0.037 | 0.074 | 2.518 |
| Ex 9 | 42/58 | 1.00 Ti | 2.80 | 68 | 30 | 96.4 | 0.201 | 0.015 | 0.016 | 0.033 | 0.069 | 2.539 |

TABLE 1-continued

| Tests | Al/Ni Alloy % by wgt | Doping agent % by wgt/Ni | Al/Ni % by wgt | Ri | Rm | S % for HMD | S % for HMI | S % for AzCHe | S % for cis- + trans-DCH | S % for AMCPA | S % for NEtHMD | S % for BHT |
|---|---|---|---|---|---|---|---|---|---|---|---|---|
| Ex 9 | 42/58 | 1.50 Ti | 2.80 | 93 | 41 | 97.0 | 0.182 | 0.050 | 0.025 | 0.032 | 0.058 | 2.149 |
| Ex 10 | 42/58 | 2.25 Ti | 2.90 | 84 | 39 | 97.4 | 0.164 | 0.039 | 0.024 | 0.031 | 0.043 | 1.975 |
| Ex 11 | 28/72 | 0.35 Ti | 3.02 | 64 | 33 | 97.8 | 0.176 | ND | 0.022 | ND | 0.017 | 1.796 |
| Ex 12 | 28/72 | 0.74 Ti | 2.94 | 94 | 39 | 98.7 | 0.257 | ND | 0.076 | ND | 0.048 | 0.920 |
| Ex 13 | 28/72 | 1.92 Ti | 3.18 | 164 | 71 | 98.4 | 0.001 | 0.021 | 0.018 | 0.005 | 0.148 | 1.451 |
| Ex 14 | 6/94 | 0.87 Ti | 3.58 | 185 | 67 | 96.6 | 0.239 | 0.043 | 0.018 | 0.028 | 0.086 | 2.851 |
| Ex 15 | 6/94 | 1.55 Ti | 3.92 | 233 | 61 | 96.8 | 0.319 | 0.045 | 0.015 | 0.032 | 0.098 | 2.700 |
| Ex 16 | 6/94 | 2.17 Ti | 4.22 | 231 | 68 | 97.6 | 0.187 | 0.203 | 0.037 | 0.013 | 0.074 | 1.937 |
| Tc 2 | 50/50 | 0.72 Cr | 7.10 | 66 | 34 | 96.6 | 0.190 | 0.020 | 0.110 | 0.004 | 0.140 | 3.015 |
| Tc 3 | 42/58 | 2.90 Cr | 8.05 | 32 | 12 | 96.2 | 0.310 | 1.260 | 0.120 | 0.032 | 0.064 | 2.025 |

TABLE 2

| Tests | Al/Ni Alloy % by wgt | Doping agent % by wgt/Ni | Al/Ni % by wgt | Ri | Rm | S % for HMD | S % for HMI | S % for AzCHe | S % for Cis- + trans-DCH | S % for AMCPA | S % for NEtHMD | S % for BHT |
|---|---|---|---|---|---|---|---|---|---|---|---|---|
| Ex 17 | 28/72 | 0.44 Cr | 2.76 | 126 | 52 | 97.6 | 0.124 | 0.227 | 0.034 | 0.016 | 0.090 | 1.873 |
| Ex 18 | 28/72 | 0.60 Cr | 3.15 | 153 | 63 | 97.4 | 0.136 | 0.147 | 0.033 | 0.027 | 0.117 | 2.171 |
| Ex 19 | 6/94 | 1.57 Cr | 3.93 | 204 | 72 | 96.8 | 0.212 | 0.145 | 0.039 | 0.008 | 0.058 | 2.756 |
| Ex 20 | 6/94 | 2.05 Cr | 3.83 | 241 | 83 | 97.4 | 0.241 | 0.160 | 0.013 | 0.032 | 0.095 | 2.036 |
| Ex 21 | 28/72 | 0.64 Ti 0.47 Cr | 2.99 | 156 | 53 | 97.9 | 0.118 | ND | 0.006 | ND | ND | 2.008 |
| Ex 22 | 28/72 | 0.89 Ti 0.24 Cr | 3.10 | 166 | 88 | 97.6 | 0.158 | 0.004 | 0.025 | 0.009 | 0.174 | 2.005 |
| Ex 23 | 28/72 | 1.52 Ti 0.16 Cr | 3.16 | 168 | 64 | 97.8 | 0.094 | 0.049 | 0.006 | 0.001 | 0.049 | 1.997 |
| Ex 24 | 6/94 | 0.80 Ti 1.13 Cr | 3.87 | 219 | 62 | 97.1 | 0.288 | 0.345 | 0.037 | 0.018 | 0.074 | 2.105 |
| Ex 25 | 6/94 | 1.40 Ti 0.92 Cr | 3.88 | 220 | 64 | 97.1 | 0.307 | 0.185 | 0.039 | 0.020 | 0.081 | 2.276 |
| Tc 4 | 50/50 | 2.05 Cr | 8.10 | 107 | 53 | 95.5 | 0.200 | ND | 0.084 | 0.014 | 0.070 | 3.100 |

We claim:

1. A process for the preparation of a Raney nickel type catalyst, said process comprising subjecting a metal alloy comprising nickel and aluminum which is free of a doping agent to an alkaline attack in the presence of a doping agent in complexed form, wherein said doping agent is at least one element selected from the group consisting of Group IIb and Group IVb to VIIb of the Periodic Classification of the Elements.

2. The process according to claim 1, wherein the doping agent is introduced into the alkaline attack medium as a solution.

3. The process according to claim 2, wherein the solution is an alkaline medium.

4. The process according to claim 3, wherein the doping agent is of the same nature and substantially of the same alkalinity as the alkaline attack medium.

5. The process according to claim 1, wherein the doping element is in the form of a complex with at least one chelating agent selected from the group consisting of carboxylic acid derivatives, trienes, amines and other appropriate sequestering agents.

6. The process according to claim 1, wherein the doping element is in the form of a complex with at least one chelating agent selected from the group consisting of tartrate, citrate, ethylenediaminetetraacetate, gluconate and fatty acid carboxylates.

7. The process according to claim 6, wherein the doping element is a tartrate.

8. The process according to claim 1, wherein the doping elements are selected from the group consisting of titanium, chromium, zirconium, vanadium, molybdenum, manganese and zinc.

9. The process according to claim 8, wherein the doping elements are titanium, chromium or zirconium.

10. The process according to claim 1, wherein the doping agent is introduced at the beginning of the alkaline attack.

11. The process according to claim 1, wherein more than one doping agent is involved during the alkaline attack on the precursor alloy.

12. A catalyst prepared by the process of claim 1, having an aluminum content, expressed by weight with respect to the weight of the nickel, of less than or equal to 6%.

13. The catalyst according to claim 12, wherein the aluminum content is less than or equal to 5%.

14. The catalyst according to claim 13, wherein the aluminum content is between 2.5% and 4.5%.

15. The catalyst according to claim 12, wherein the doping agent/nickel ratio is between 0.05% and 10% by weight.

16. The catalyst according to claim 15, wherein the doping agent/nickel ratio is between 0.1% and 5% by weight.

17. The catalyst according to claim 16, wherein the doping agent/nickel ratio is between 0.3% and 3.5% by weight.

18. A process for the hydrogenation of nitriles to amines, said process comprising exposing a nitrile to the catalyst of claim 1 in a liquid reaction medium to obtain an amine.

19. The process according to claim 18, wherein the nitrile is a dinitrile having formula (I):

NC—R—CN     (I)

wherein R represents a linear or branched alkylene or alkenylene group having from 1 to 12 carbon atoms or a substituted or unsubstituted arylene or aralkylene or aralkenylene group.

20. The process according to claim 19, wherein R represents a linear or branched alkylene radical having from 2 to 6 carbon atoms.

21. The process according to claim 18, wherein the nitrile is selected from the group consisting of adiponitrile, methylglutaronitrile, ethylsuccinonitrile, malononitrile, succinonitrile, glutaronitrile and mixtures thereof.

22. The process according to claim 18, wherein the concentration of nitrile in the total reaction medium is between 0.001% and 30% by weight.

23. The process according to claim 22, wherein the concentrate of nitrile is between 0.1% and 20%.

24. The process according to claim 18, further comprising adding a base selected from the group consisting of LiOH, NaOH, KOH, RbOH and CsOH.

25. The process according to claim 18, wherein the liquid reaction medium comprises water.

26. The process according to claim 25, wherein the water comprises less than or equal to 20% by weight of the total liquid reaction medium.

27. The process according to claim 26, wherein the base comprises between 0.1% and 15% by weight of the total liquid reaction medium.

28. The process according to claim 18, wherein the liquid reaction medium contains a targeted amine.

29. The process according to claim 28, wherein the targeted amine is introduced into the liquid reaction medium in a proportion of 50 to 99% by weight with respect to the weight of the total liquid reaction medium.

30. The process according to claim 29, wherein the targeted amine is introduced into the liquid reaction medium in a proportion of 60 to 97% by weight.

31. The process according to claim 18, wherein the liquid reaction medium contains an alcohol and/or amide.

32. The process according to claim 31, wherein the alcohol is selected from the group consisting of methanol, ethanol, propanol, isopropanol, butanol, glycols, polyols and mixtures thereof.

33. The process according to claim 32, wherein the glycol is selected from the group consisting of ethylene glycol and propyleneglycol.

34. The process according to claim 31, wherein the amide is dimethylformamide or dimethylacetamide.

35. The process according to claim 24, wherein the base is present in an amount greater than or equal to 0.1 mole/kg of catalyst.

36. The process according to claim 35, wherein the base is present in an amount between 0.1 and 2.0 mole/kg of catalyst.

37. The process according to claim 36, wherein the base is present in an amount between 0.5 and 1.5 mole/kg of catalyst.

38. The process according to claim 24, wherein the base is present in an amount greater than or equal to 0.05 mole/kg of catalyst.

39. The process according to claim 38, wherein the base is present in an amount between 0.1 and 10.0 mole/kg of catalyst.

40. The process according to claim 39, wherein the base is present in an amount between 1.0 and 8.0 mole/kg of catalyst.

41. The process according to claim 18, wherein the hydrogenation is carried out at a temperature which is less than or equal to 120° C.

42. The process according to claim 41, wherein the hydrogenation is carried out at a temperature which is less than or equal to 100° C.

43. The process according to claim 19, wherein the dinitrile is adiponitrile which is converted to hexamethylenediamine.

44. The process according to claim 19, wherein the dinitrile is adiponitrile which is converted to aminocapronitrile.

* * * * *